(12) United States Patent
Breur

(10) Patent No.: US 8,278,226 B2
(45) Date of Patent: Oct. 2, 2012

(54) ANTIFOULING FIBRE COATINGS FOR MARINE CONSTRUCTIONS

(75) Inventor: Hendrik Jacobus Arie Breur, Hoofddorp (NL)

(73) Assignee: Materials Innovation Centre B.V., Hoofddorp (NL)

( * ) Notice: Subject to any disclaimer, the term of this patent is extended or adjusted under 35 U.S.C. 154(b) by 885 days.

(21) Appl. No.: 12/293,548

(22) PCT Filed: Mar. 16, 2007

(86) PCT No.: PCT/NL2007/050106
§ 371 (c)(1), (2), (4) Date: Nov. 28, 2008

(87) PCT Pub. No.: WO2007/108679
PCT Pub. Date: Sep. 27, 2007

(65) Prior Publication Data
US 2010/0227111 A1 Sep. 9, 2010

(30) Foreign Application Priority Data
Mar. 21, 2006 (EP) .................................. 06111501

(51) Int. Cl.
*B32B 5/00* (2006.01)
*B32B 33/00* (2006.01)
*B01J 19/00* (2006.01)

(52) U.S. Cl. .............. 442/123; 442/59; 428/92; 428/96; 427/457

(58) Field of Classification Search ................ 114/67; 428/85–94, 95–100
See application file for complete search history.

(56) References Cited

U.S. PATENT DOCUMENTS 3,554,154 A 1/1971 Thomas
4,923,730 A * 5/1990 Taniguchi et al. .............. 428/92

FOREIGN PATENT DOCUMENTS

| EP | 0 353 095 A2 | | 1/1990 |
| WO | WO 92/07037 | * | 4/1992 |
| WO | 93/25432 A | | 12/1993 |

* cited by examiner

*Primary Examiner* — Jennifer A Steele
(74) *Attorney, Agent, or Firm* — Young & Thompson

(57) ABSTRACT

A fiber-coated marine material has antifouling properties, without necessarily containing bioactive agents. At least a part of the marine material is covered by piles of fibers having a thickness of at least 50 μm and a fiber length of at least 3 mm. The thickness-to-length ratio of the fibers is at least 0.010, and the piles of fibers have a density lower than 40 fibers/mm². The fiber coating can be directly applied onto the marine material, such as ropes and construction parts, or can be present on sheets which can be applied on the marine equipment.

19 Claims, No Drawings

ANTIFOULING FIBRE COATINGS FOR MARINE CONSTRUCTIONS

FIELD OF THE INVENTION

The invention pertains to a fibre-coated marine material, which prevents unwanted fouling organisms from attaching and growing on immersed structures that come in contact with water, especially sea water. The invention also pertains to the preparation of such a fibre-coated marine material, and to a fibre-coated sheet applicable for making an antifouling marine construction.

BACKGROUND OF THE INVENTION

On underwater structures and on ship's hulls which are exposed to sea and/or fresh water, attachment and growth of marine organisms cause severe economic losses because of the increased friction and therefore increased consumption of fuel, or increased resistance to waves or currents (for static structures such as off-shore rigs), and because of decreased possible operation time. Traditionally major users of ships have attempted to resist fouling by painting hulls with paints containing e.g. copper or tributyltin, a tin-based compound. These paints are highly toxic and the toxic substances leach into the water, killing marine life.

Over the years several types of biocide-free antifouling paints have entered the market to meet the growing needs for environmentally acceptable alternatives. Some interest is also given to fibre coatings. By planting pines or thin fibres on a surface of marine material, settling of fouling organisms is deterred. The flexible fibres naturally sway in the water, thus creating a swaying fur-like surface, while it is said that spores, zoospores or larval organisms of algae and shellfishes generally plant particularly to relatively hard and scarcely swaying matter.

According to B. T. Watermann et al. *"Bioassays and selected chemical analysis of biocide free antifouling agents"* Chemosphere 60 (2005) 1530-1541, a fibre coating typically consists of short fibres in a dense pattern (200-500 fibres/mm$^2$). First, an adhesive is applied, which serves as glue for the fixation of fibres. The fibres are then electrostatically charged and sprayed into the wet adhesive layer so that they remain perpendicularly oriented in the adhesive.

EP-A312.600 relates to a fur-like fibre-coated marine material preventing attachment of algae and shellfishes, which material is characterized in that it is covered by a number of piles comprised of a fine fibre of 5 denier or less. A denier unit is sometimes used to express the fineness of a yarn, and equals the mass in g per 9 km of yarn. It is mentioned in EP-A-312.600 that a denier greater than 5 is undesirable, because the fibre would sway less in water and further produce an uneven surface, which would attract the attachment of algae and shellfishes. Instead, it teaches the use of fibres of 1.5 denier or less, because of reasons of effect, ease of production, economic reasons and ease of handling. The effect of these small fibres on adherence of algae and shellfishes is believed to relate to the swaying properties of the fibres. The ability of the piles to sway by tidal current and wave would be controlled by the length and thickness of the piles.

Further, EP-A-353.095 discloses an antifouling sheet comprising fibre elements which are about 10-300 µm in diameter and about 10-30 mm long. The fibre elements are relatively long and the ratio of thickness versus length is selected such as to obtain a flexible fur-like surface which enables free swaying movements in water.

WO-A-93/25432 teaches the use of fibres flock with a high density of thin, short fibres, for antifouling of marine constructions. It mentions a density of 50-300 fibres/mm$^2$, a fibre thickness of less than 0.1 mm, and a pile length of 0.5-5 mm, but is silent on any other physical property of the fibre flock, and on the process for obtaining such fibres. It is at least clear that with current techniques and materials it is not possible to produce fibres having combinations of densities and thicknesses in all parts of the ranges mentioned therein. The minimum density of 50 fibres/mm$^2$, and the preferred minimum density of 150 fibres/mm$^2$ indicates that very thin and short fibres are proposed, of the order of maximum 1 mm in length and a thickness smaller than 10 denier.

None of these existing swaying fur-like coatings fully prevent attachment and growth of barnacles, algae, seaweeds, shellfish and the like. Especially growth of algae and other soft fouling species cannot be reduced with similar efficiency as for instance achieved with biocidal paints.

DESCRIPTION OF THE INVENTION

It is an object of the invention to provide a fibre-coated marine material with improved antifouling properties, without requiring any biocide materials, and which fibre-coated material protects the submerged marine construction from settling down of all kinds of organisms.

It is now found that the efficacy of the antifouling coating can be improved by selecting fibres having a thickness of 50 µm or more, preferably 60 µm or more, a fibre length of at least 3 mm, and wherein the coating contains piles of fibres having a density lower than 40 fibres/mm$^2$. For the sake of comparison, a thickness of 60 µm corresponds to approximately 30 denier. The selection of relatively short and thick fibres creates a surface, which is better characterized as being "thorn-like", rather than the fur-like fibre-coatings nowadays applied. In contrast to the teachings in the art, it is observed that the effectiveness of the technology increases markedly going towards stiffer piles.

The invention thus relates to a fibre-coated marine material having antifouling properties, wherein at least part of the marine material is covered by piles of fibres having a thickness of at least 70 µm, a fibre length of at least 3 mm, and wherein the piles of fibres have a density lower than 40 fibres/mm$^2$.

With "antifouling" is meant the prevention of attachment and growth of aquatic organisms from (partly) underwater surfaces where they have a negative influence on the surface's physical attributes. An important group of animals that is to be prevented from settlement comprises shellfish such as mussels and oysters, barnacle and the like, and larvae thereof, tubeworms, ascidians, hydrozoans and bryozoans. The fibre material is also used in avoiding plants as algae, seaweed, and spores and zoospores thereof, from taking root on the marine constructions.

In the context of the invention "marine material" is intended to comprise materials related to objects moving in an aqueous medium meeting a resistance of flow due to friction, and marine constructions, which at least partially reach under the surface of water. A non-exhaustive list of marine materials suitable for fibre coating comprises net, rope, buoy, marker, etc. and further equipment materials of ship, hull and port and harbour, and those concerned with water equipment and articles such as pipe, water distributing channel and ditch disposed in sea, river, lake and port and harbour. In a particular embodiment, the fibre coatings are deployed in the protection of static marine constructions, such as platforms, oil rigs, mooring posts. In another embodiment, the fibres are applied on ships, boats, buoys and other floating equipment.

The marine material is covered with the fibres of the invention for the greater part of its surface area, preferably at least 75%, more preferably at least 90%.

All sorts of fibre-forming materials may be used to create a thorn-like surface on the marine material. Both hydrophilic and hydrophobic polymers can be employed. The fibres are commonly composed of polyester, polyamide or polyacryl, including polyesters such as poly(ethylene)terephthalate and poly(butylene)terephthalate, polyamides represented by nylon 6, 11, 12, 66 and 610, but also polyurethane, (modified) polyvinyl alcohol), polyalkylene such as polyethylene or polypropylene or modified (copolymerized) forms thereof, and rayon may be applied. The fibres may also comprise modifications, copolymers or mixtures of the afore-mentioned types. The fibres preferably comprise polyethylene and/or polypropylene, or copolymers thereof. In case durability is required, polypropylene may preferably be employed.

Because of the increased effectiveness of the fibres of the invention, these may be applied to the surface of a marine construction without the requirement of biocidal agents, but can be used in combination with, (lower) concentrations of bioactive compounds such as conventional tin-based, copper-based, zinc-based or other anti-fouling agents. In a preferred embodiment, however, the marine material has a fibre layer which is free of biocide materials and free of materials suspected of having biocidal properties.

The fibre thickness is preferably between 60 and 150 µm, more preferably in the range of 70-120 µm. These thicknesses apply to average values. A certain percentage (e.g. up to 10%) outside these ranges will not detract from the effectiveness of the fibre. The fibre length is typically between 3 and 30 mm. However, the thickness and length cannot be chosen independently from one another; the combination of fibre thickness and fibre length has to yield a relatively stiff, thorn-like fibre. High fibre lengths are to be avoided, as it may result in swaying motion, and could only be compensated by extending the thickness of the fibres. On the other hand, too short a fibre length may not have the required "thorn"-effect either, but result in a smooth surface not preventing organisms from settling. The other way around applies for the fibre thickness. In addition, a high fibre length and/or thickness adds surplus weight and costs. Preferably the fibre length is less than 20 mm, and optimally, the maximum length is less than 10 mm. The desired fibre length can be achieved by conventional means such as cutting.

In order to ensure sufficient pile stiffness, the ratio of the thickness to the length of the fibres is preferably between 0.010 and 0.040, more preferably between 0.012 and 0.030, most preferably between 0.015 and 0.025, in particular more than 0.016. If the ratio is too low, the piles may become flexible and result in swaying matter underwater. Swaying motion by current and waves is to be avoided, because it is found to give unsatisfactory prevention of attachment and growth of especially algae and barnacles. Too high a ratio results in the loss of the thorn-like character, and would also reduce the inhibitive effect of the fibres.

Best results are obtained if the marine material is covered by piles having fibre densities of 10-35 fibres/mm$^2$, in particular in the range of 15-30 fibres/mm$^2$. The actual density of fibres in the piles is determined by the combination of pile length and fibre thickness.

The invention further relates to a method for providing a marine material with an antifouling top layer covered at least partly by the piles of fibres of the invention. These piles may be generated by any manufacturing method known in the art, and could be applied directly to the marine material. Several manufacturing methods are described in EP-A-312.600.

In one embodiment the thorn-like surface is provided by first applying a water-resistant adhesive, for instance an epoxy or a polyurethane, to the marine material to form an adhesive layer, where after the selected fibres are electrostatically charged and brought into contact with the adhesive layer, for instance using spraying techniques.

In another embodiment, the piles may also be applied as a sheet. Therefore, the invention also relates to a sheet comprising a base member and the fibres of the invention attached thereto. The base member can be made of any kinds of material, e.g. polyester, polyethylene, polypropylene, vinyl, textile and paper-like materials.

Alternatively, a yarn could be produced having piles in the form of a bundle of fibres, which yarns could be subjected to a net weaving or rope making process. The woven fabric may then be applied to the marine construction.

The method of fabrication is adapted to the particular use of the fibres as a coating, sheet, rope, net or fabric, and can be applied to all water-wetted surfaces. The coating can be adapted to the dimensions of the expected fouling particles and the expected flow across the underwater surface by adequate choice of its material and shape.

Where a 3D object is covered with a thorn-like surface of the invention, a guiding system, fixing the object in the flocking machine to avoid contact of the object with the installation is needed. A first step of providing a layer of adhesive to the object may be performed by e.g. spraying, dipping or rolling. In order to save adhesive material in case of spraying of netting, wasted adhesive may be collected below the netting. In case of dipping, care must be taken to avoid inhomogeneous layer formation, for instance using air-jetting. Foamed adhesives may be used. Also, the rheology of the adhesive can be adjusted.

In order to achieve an evenly distributed thorn-layer, it is found useful to optimize flow potential and/or the distance between the flow outlet and the object to be covered. The thorns may also be applied in two steps: first a low density but evenly distributed flock of thorns is provided to the object, where after a more dense coverage is achieved with sequential flocking steps. Every step may have its own optimal velocity and outlet-object distance. It is considered to be within the skilled person's ambit to determine the optimal conditions.

It may further be helpful to apply the thorns while the surface is vertically positioned. Also, the object may be oppositely charged, not necessarily of same absolute magnitude. Generally, the object is grounded.

In case of meshes, an airflow, or a second (grounded or oppositely charged) object behind the mesh may be applied to improve the pass rate. The thorns may be provided from both sides simultaneously.

The marine material may be coloured, in order to minimize photosynthesis-supported growth of algae. The preventive effect of the thorn-like surface may further be enhanced by selecting pigments in the fibre-layer which scarcely absorb the light in the region of wave length suitable for photosynthesis of algae tending to attach in the water where the material is used. Ultraviolet ray absorbents may also be applied to prevent degradation caused by ultraviolet radiation and/or to improve durability of the fibre-coated material. If desired the fibre stiffness may be increased by using additives (e.g. nano-structured particles).

Example 1

PVC panels 30×20 cm$^2$ were coated with thorns using a water resistant polyurethane glue as adhesive and several different types of thorns made of polyamide (lengths>3 mm, thicknesses>60 μm) with a density of 20 thorns/mm². Electrostatic flocking was used for the application. After curing of the glue, the PVC panels were exposed to seawater for 10 months. Plain PVC panels were exposed as well. All materials with described thorns remained free of fouling. Panels without described thorns fouled, a.o. with mussels, barnacles and algae.

Comparative Example I

PVC panels 30×20 cm² were coated with thorns using a water resistant polyurethane glue as adhesive and several different types of thorns made of polyamide (length 0.5 and 2 mm, thicknesses<60 μm) with a density of 20 thorns/mm². Electrostatic flocking was used for the application. After curing of the glue, the PVC panels were exposed to seawater for 10 months. All materials with described thorns fouled, with mussels, barnacles and algae.

Comparative Example II

In a large research project funded by the Deutsche Bundesstiftung Umwelt, presented at the *International Symposium on Biocide-free Antifouling Coatings Performance, Prospects and Regulations*, in November 2003, "swaying" fibres were used to deter fouling. Fibre lengths were 1.0 and 1.2 mm and fibre density was 200 fibres/mm². Fouling coverage after some time reached up to 100% with hard fouling (e.g. barnacles) reaching up to 70% coverage, showing that thin fibres which exhibit a "swaying" motion are not effective against fouling.

Example 2

Flexible knotless netting with hexagonal mesh and sample size 20×20 cm² made of Nylon and Dyneema, and a sample 20×20 cm² of stiff netting material with square meshes, made of PVC, were coated with thorns using a water resistant polyurethane glue as adhesive and thorns made of polyamide (lengths>3 mm, thicknesses>60 μm) with a density of 20 thorns/mm². Electrostatic flocking was used for the application. After curing of the adhesive, the netting samples were exposed to seawater for 8 months, together with reference netting samples without the described thorns, All materials with thorns remained free of fouling, whereas the reference netting material fouled with soft fouling like algae, hydrozoans and ascidians and with hard fouling like mussels and barnacles.

The invention claimed is:

1. A fibre-coated marine material having antifouling properties, wherein:
   at least part of said marine material is covered by piles of fibres having a thickness of at least 50 μm and a fibre length of at least 3 mm,
   said fibres have a thickness-to-length ratio of at least 0.010, and
   said piles of fibres have a density of 10-35 fibres/mm².

2. The fibre-coated marine material according to claim 1, wherein said fibres have a thickness between 70 and 150 μm.

3. The fibre-coated marine material according to claim 1, wherein said fibre length is between 3 and 10 mm.

4. The fibre-coated marine material according to claim 1, wherein the thickness-to-length ratio of said fibres is between 0.015 and 0.025.

5. The fibre-coated marine material according to claim 1, wherein the fibres comprise polyalkylene or modified forms thereof.

6. The fibre-coated marine material according to claim 1, wherein the material is essentially free of bioactive agents.

7. The fibre-coated marine material according to claim 1, further comprising a bioactive agent applied to the material.

8. A method for providing a marine material having an antifouling top layer, comprising providing the marine material with piles of fibres having a thickness of at least 50 μm and a fibre length of at least 3 mm attached thereto, wherein
   said fibres have a thickness-to-length ratio of at least 0.010, and
   said piles of fibres have a density of 10-35 fibres/mm².

9. The method according to claim 8, wherein a water-resistant adhesive is first applied to said marine material to form an adhesive layer, and then said fibres are electrostatically charged and brought into contact with said adhesive layer.

10. A fibre-coated sheet suitable for giving a marine material antifouling properties, said sheet comprising:
    a base member, and
    piles of fibres having a thickness of at least 50 μm and a fibre length of at least 3 mm attached thereto,
    wherein said fibres have a thickness-to-length ratio of at least 0.010, and
    said piles of fibres have a density of 10-35 fibres/mm².

11. The fibre-coated sheet according to claim 10, wherein said base member comprises a foil of polymeric material.

12. The fibre-coated marine material according to claim 2, wherein said fibre length is between 3 and 10 mm.

13. The fibre-coated marine material according to claim 2, wherein the thickness-to-length ratio of said fibres is between 0.015 and 0.025.

14. The fibre-coated marine material according to claim 2, wherein the fibres comprise polyalkylene or modified forms thereof.

15. The fibre-coated marine material according to claim 2, wherein the material is essentially free of bioactive agents.

16. The fibre-coated marine material according to claim 2, further comprising a bioactive agent applied to the material.

17. The fibre-coated marine material according to claim 1, wherein said piles of fibres have a density of 15-30 fibres/mm².

18. The method according to claim 8, wherein said piles of fibres have a density of 15-30 fibres/mm².

19. The fibre-coated sheet according to claim 10, wherein said piles of fibres have a density of 15-30 fibres/mm².

* * * * *